United States Patent
Dolatshahi-Pirouz et al.

(10) Patent No.: US 11,427,709 B2
(45) Date of Patent: Aug. 30, 2022

(54) PROTEIN-BASED WATER INSOLUBLE AND BENDABLE POLYMER WITH IONIC CONDUCTIVITY

(71) Applicant: Danmarks Tekniske Universitet, Kgs. Lyngby (DK)

(72) Inventors: Alireza Dolatshahi-Pirouz, Kgs. Lyngby (DK); Firoz Babu Kadumudi, Kgs. Lyngby (DK); Mehdi Mehrali, Kgs. Lyngby (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 17/277,974

(22) PCT Filed: Sep. 20, 2019

(86) PCT No.: PCT/EP2019/075339
§ 371 (c)(1),
(2) Date: Mar. 19, 2021

(87) PCT Pub. No.: WO2020/058481
PCT Pub. Date: Mar. 26, 2020

(65) Prior Publication Data
US 2021/0309857 A1    Oct. 7, 2021

(30) Foreign Application Priority Data
Sep. 21, 2018  (EP) .................................. 18195996

(51) Int. Cl.
*C08L 89/00*   (2006.01)
*G06F 3/044*   (2006.01)
(Continued)

(52) U.S. Cl.
CPC ............ *C08L 89/00* (2013.01); *A61B 5/1107* (2013.01); *A61B 5/6801* (2013.01); *C08K 3/16* (2013.01);
(Continued)

(58) Field of Classification Search
CPC .... C08L 89/00; C08L 2201/10; G06F 3/0444; G06F 3/0445; A61B 5/6801;
(Continued)

(56) References Cited

FOREIGN PATENT DOCUMENTS

| CN | 103762014 A | 4/2014 | |
|---|---|---|---|
| CN | 106580256 A | 4/2017 | |
| CN | 108396425 | * 8/2018 | ............... D02G 3/04 |

OTHER PUBLICATIONS

English machine translation of CN 108396425 (Year: 2018).*
(Continued)

*Primary Examiner* — John E Uselding
(74) *Attorney, Agent, or Firm* — Knobbe, Martens, Olson & Bear, LLP

(57) ABSTRACT

An ionic conductive, stretchable, and flexible transparent material includes silk fibroin, a nanomaterial, and an electrolyte. The material can be recycled. A flexible surface capacitive touch panel and a flexible motion sensor can both be based on the ionic conductive, stretchable, and flexible transparent material. The ionic conductive, stretchable, and flexible transparent material shows many desirable properties, such as a good crystallinity, transparency, mechanical strength, recyclability, optical transparency, and electrical sensitivity. The material shows chemical and thermal stability, in addition to excellent dimensional stability.

17 Claims, 12 Drawing Sheets

(51) Int. Cl.
  *A61B 5/11* (2006.01)
  *A61B 5/00* (2006.01)
  *C08K 3/16* (2006.01)
  *C08K 3/34* (2006.01)
(52) U.S. Cl.
  CPC ............ *C08K 3/346* (2013.01); *G06F 3/0444* (2019.05); *G06F 3/0445* (2019.05); *A61B 2562/0214* (2013.01); *C08K 2003/162* (2013.01); *C08K 2003/166* (2013.01); *C08K 2201/001* (2013.01); *C08K 2201/011* (2013.01); *C08L 2201/10* (2013.01); *C08L 2203/20* (2013.01); *G06F 2203/04102* (2013.01); *G06F 2203/04103* (2013.01)
(58) Field of Classification Search
  CPC ................ A61B 5/1107; C08K 3/346; C08K 2003/162; C08K 2003/166; C08K 2201/001; C08K 2201/011; C08K 3/16
  See application file for complete search history.

(56) References Cited

OTHER PUBLICATIONS

Yun et al. Microporous Carbon Nanoplates from Regenerated Silk Proteins for Supercapacitors. Adv. Mater. 2013, 25, 1993-1998 (Year: 2013).*
International Search Report and the Written Opinion for International Patent Application No. PCT?EP2019/075339, dated Dec. 20, 2019 in 13 pages.
Database WPI, Week 201738, Thomson Scientific, London, GB; AN 2017-285651, XP002789925, 2017.
Database WPI, Week 201444, Thomson Scientific, London, GB; AN 2014-L78599, XP002789926, 2014.

* cited by examiner a)

b)

c)

a)

b)

PROTEIN-BASED WATER INSOLUBLE AND BENDABLE POLYMER WITH IONIC CONDUCTIVITY

CROSS-REFERENCE TO RELATED APPLICATIONS

This application is the U.S. National Phase under 35. U.S.C. § 371 of International Application PCT/EP2019/075339, filed Sep. 20, 2019, which claims priority to European Patent Application No. 18195996.6, filed Sep. 21, 2018. The disclosures of the above-described applications are hereby incorporated by reference in their entirety.

TECHNICAL FIELD

Disclosed herein is an ionic conductive, stretchable, and flexible transparent material comprising silk fibroin; a nanomaterial, such as a nano clay, a carbon nanomaterial, or a Mxene; and an electrolyte, and a method of recycling said material. Additionally disclosed is a flexible surface capacitive touch panel and a flexible motion sensor both based on the ionic conductive, stretchable, and flexible transparent material.

BACKGROUND ART

The replacement of inorganic electronic components with organic counterparts can transform hard and rigid electronics into devices that can conform to the curvatures of the human body. This can ultimately yield a number of exciting human-machine-interactions. Unfortunately, organic electronics still require modifications to enable them to resist the many demanding scenarios in nature and induced by the human body.

Ionic conductors can generate a number of exciting electronic devices, and many organic electronic materials has been transformed into such mediators of electricity. This was thought as a solution for the above bottleneck through the manufacture of water-insoluble, thermally and chemically stable protein films with high ionic conductivity.

In simple terms, ionic conductors can be defined as materials that conduct electricity through the passage of ionic carries such as $Li^+$, $Na^+$, $K^+$, $Cl^-$, $Mg^{2+}$, and $Ca^{2+}$. Ionic conductors have e.g. been used in Li-Ion battery technology. Even though ionic conductors has pushed the field of electronics, there is still drawbacks that need to be addressed in the future.

Most of the devices within ionic conductors have been made from polyacrylamide. However, polyacrylamide is hazardous for habitats and for humans. This is due to the release of acrylamide into the environment. Polyacrylamide is a synthetic polymer and it is therefore not considered a green option.

Polysaccharides such as alginate, starch, hyaluronic acid, and chitosan are possible alternatives. Unfortunately, some of these polymers typically display a number of mechanical shortcomings in a cross-linked and solidified state.

Other alternative materials are protein-based materials such as keratin and collagen, because these materials have low-cost, high flexibility, and display desirable electrical properties. Unfortunately, they display low environmental stability. Additionally, they have insufficient mechanical integrity to become amenable as substrates for touchscreens and electronic displays.

Other flexible conductors, which are based on serpentine-configured metallic wires, carbon nanotubes, graphene, silver nanowires, gold nano-sheets, conducting polymers, and metal oxides, have shown great interest in the field of electronics. Unfortunately, many of these also display a number of shortcomings, including low transparency, environmental toxicity, inability to operate at large frequencies, biocompatibility, insufficient conductivity when bended or stretched, and a high manufacturing cost.

For the above reasons, material scientists and electrical engineers currently find themselves in the quest for green solutions with sufficient mechanical integrity and operational stability.

SUMMARY

Disclosed herein in a first aspect is an ionic conductive, stretchable, and flexible transparent material comprising silk fibroin, a nanomaterial, and an electrolyte, wherein the nanomaterial is present in an amount of 3 to 24 parts by weight for every 100 parts by weight of the silk fibroin.

The term 'an ionic conductive material' is to be understood as a material, which is able to conduct electrical current through the material and the electrical current is transported by means of ions. An ionic conductive material as disclosed here is normally a material, which can conduct at least 1 µA of electrical current through the material.

The term 'a stretchable material' is to be understood as a material, which is able to stretch at least 1% of its length before breaking. A stretchable material as disclosed here is normally a material, which has an average modulus of at least 100 kPa.

The term 'a flexible material' is to be understood as a material, which is capable of being bent without breaking. A flexible material as disclosed here is normally a material, which is capable of being bent at least 30 degrees without breaking. A flexible material as disclosed here is normally a material, which has an average flexible modulus of at least 100 kPa.

The term 'a transparent material' is to be understood as a material, which allows light to pass through so that objects behind can be distinctly seen. A transparent material as disclosed here is normally a material, which allows at least 50% of light with a wavelength at 400 nm to pass through the material.

The material according to the first aspect shows many of the desired properties within the field of ionic conductors. These properties include a good crystallinity, transparency, mechanical strength, recyclability, optical transparency, and electrical sensitivity. Additional, the disclosed material shows chemical and thermal stability, in addition to excellent dimensional stability.

The material further shows stable performance in aqueous and chemically active environments.

The previously observed problems with materials having low transparency, environmental toxicity, inability to operate at large frequencies, biocompatibility, insufficient conductivity when bended or stretched, and a high manufacturing cost, is avoided by the material according to the first aspect.

The use of proteins are considered a greener choice than many of the hazardous components currently used in the field of electronics. A combination of proteins with other properties such as flexibility, transparency, mechanical toughness, electrical conductivity, chemical and thermal stability, uncover a range of ground-breaking opportunities in the field of flexible and green electronics. Protein-based silk fibers has an incredible portfolio of properties. These include good biocompatibility, nontoxicity, recyclability, thermoelectricity, transparency, thermal stability, and incredible mechanical strength.

Nanomaterial, such as e.g. nano clay, is relatively cheap materials and in combination with various proteins they can improve the mechanical strength, electrical conductivity, and water stability of the final protein film. Nano clay is also biocompatible and nontoxic.

Disclosed here in a second aspect is a method of recycling an ionic conductive, stretchable, and flexible transparent material comprising silk fibroin, a nanomaterial, and an electrolyte, wherein the nanomaterial is present in an amount of 3 to 24 parts by weight for every 100 parts by weight of the silk fibroin wherein the recycling method comprises the steps of:
  mixing a dissolving solution comprising lithium bromide in a concentration of at least 8 molar;
  adding the ionic conductive, stretchable, and flexible transparent material to the dissolving solution;
  dissolving the ionic conductive, stretchable, and flexible transparent material in the dissolving solution hereby creating a solid phase and a liquid supernatant phase;
  centrifuging the dissolving solution and collecting the supernatant phase wherein the silk fibroin is contained; and
  purifying the supernatant phase comprising the silk fibroin by dialysis against deionized water for at least 10 hours, such as at least 14 hours, such as at least 18 hours, such as at least 24 hours.

Having a method, wherein the materiel is recycled, is a green option, as the recycled material can be reused in the production of new materiel, hereby saving resources and not throwing out unnecessary amounts of precious materiel. Additionally, reusing parts of the material may contribute to a lower manufacturing cost of the material. Additionally, a method wherein the materiel is recycled, is also considered a green option because the recycling process can minimize the accumulation of electronic waste materials, which pose a huge environmental threat.

Disclosed here in a third aspect is a flexible surface capacitive touch panel comprising a touch panel material defining a touch panel surface area, wherein the touch panel material comprises:
  silk fibroin;
  a nanomaterial, wherein the nanomaterial is present in an amount of 3 to 24 parts by weight for every 100 parts by weight of the silk fibroin, and
  an electrolyte, wherein the electrolyte is present in an amount above 2 parts by weight for every 100 parts by weight of the silk fibroin.

The touch panel material shows many of the desired properties within the field of ionic conductors. These properties were also described in regards to the material disclosed in the first aspect. The touch panel materials can be configured in to a plain or patterned form and can be used for touch or hovering touch applications. To envisage the patterned flexible touch panel, the casting solution containing silk fibroin and a nanomaterial can be injected into the patterned channels of elastomer films e.g. polydimethylsiloxane (PDMS). In this application, the current or capacitance change can be measured while touch or hovering touch using a single layer or multi-layered films separated by a dielectric material. Furthermore, the material disclosed in the third aspect shows excellent flexibility, while maintaining good conductivity, hereby creating a flexible touch panel.

Disclosed here in a fourth aspect is a flexible motion sensor comprising a flexible motion sensor material defining a flexible motion sensor surface area, wherein the flexible motion sensor material comprises:
  silk fibroin,
  a nanomaterial, wherein the nanomaterial is present in an amount of 3 to 24 parts by weight for every 100 parts by weight of the silk fibroin, and
  an electrolyte, wherein the electrolyte is present in an amount above 2 parts by weight for every 100 parts by weight of the silk fibroin.

The flexible motion sensor material shows many of the desired properties within the field of ionic conductors. These properties were also described in regards to the material disclosed in the first aspect. The material furthermore provides good flexibility and conductivity.

Disclosed here in a fifth aspect is the use of a flexible motion sensor comprising a flexible motion sensor material defining a flexible motion sensor surface area for measuring/detecting movement of a joint, wherein the flexible motion sensor material comprises:
  silk fibroin;
  a nanomaterial, wherein the nanomaterial is present in an amount of 3 to 24 parts by weight for every 100 parts by weight of the silk fibroin, and
  an electrolyte, wherein the electrolyte is present in a concentration above 2 parts by weight for every 100 parts by weight of the silk fibroin.

A flexible motion sensor material as disclosed herein is flexible and may be attached to any part of the body. Here through, it maybe monitor the motion of almost any part of the body. In general, its application may include healthcare monitoring, virtual gaming, or disease diagnosis. It can also be expanded into a motion-sensitive glove, which may assist surgeons, e.g. for monitoring the Parkinson's disease, piano players, or concert players to improve their performance. In virtual gaming this glove may be used to transmit motions into movements in the game and hereby hold the promise of interfacing the use with the virtual world of gaming. In another application, it can be used inside the body to monitor the movements of the organs. In an example, the flexible motion sensor may be attached/adhered to the heart with or without the aid of an adhesive layer, which can monitor the physiological movements (expansion and contraction) of the cardiac tissue.

Disclosed here in a sixth aspect is a method for production of an ionic conductive, stretchable, and flexible transparent material comprising steps of:
  dissolving silk fibroin in a solution comprising lithium bromide to obtain a silk fibroin solution, wherein the lithium bromide is in a concentration above 8 molar, such as above 9 molar;
  heating the silk fibroin solution to a temperature above 50° C., such as above 60° C., for at least 3 hours;
  dialyzing the silk fibroin solution against deionized water for at least 24 hours;
  centrifuging the silk fibroin solution to remove impurities and collecting the supernatant;
  adjusting the pH of the supernatant of the silk fibroin solution to a pH above 10, such as a pH of 11;
  dissolving an electrolyte in the desired amount in the supernatant of the silk fibroin solution;
  dissolving a nanomaterial in the desired amount in the supernatant of the silk fibroin solution; and
  casting the silk fibroin solution at a required size at a temperature above 30° C. for at least 18 hours, hereby obtaining an ionic conductive, stretchable, and flexible transparent material comprising silk fibroin, the nanomaterial, and the electrolyte.

The naturally derived polymer, silk fibroin, may be transformed via a simple casting procedure into a flexible and eco-friendly ionic film. Silk proteins retrieved from *Bombyx mori* cocoons may be used for producing the silk fibroin.

Silk fibroin can interact with nanomaterial to improve the mechanical properties of the ionic conductive, stretchable, and flexible transparent material. The process disclosed herein may additionally aid the silk fibroin to be more stable in water.

Disclosed here in a seventh aspect is a method for production of a flexible surface capacitive touch panel, the method comprising the step of:
- affixing at least two platinum or copper plates on the ionic conductive, stretchable, and flexible transparent material obtained by the method the sixth aspect, using silver epoxy paste, hereby obtaining a flexible surface capacitive touch panel, wherein the flexible surface capacitive touch panel is adapted for operating at an AC voltage of −0.5 to 0.5 V and within a frequency range of 10 to 40 kHZ, wherein an AC current or capacitance response from a finger-touch is measurable using an oscilloscope.

A flexible surface capacitive touch panel as disclosed herein operates at very low voltage and works at different frequencies, which means that it delivers stable performances in the kilohertz regime.

Disclosed here in an eighth aspect is a method for production of a flexible motion sensor comprising the steps of:
- connecting copper wires to both ends of the ionic conductive, stretchable, and flexible transparent material obtained by the method according to the sixth aspect, using conductive silver epoxy paste, hereby obtaining a flexible motion sensor, wherein the flexible motion sensor is adapted for operating at 10 kHz by applying an AC voltage ranging from −0.5 to 0.5 V;
- attaching the flexible motion sensor to various moving parts of a body such as a finger, a wrist, a shoulder, an ankle, an elbow, or a knee, by means of cloth adhesive tape or adhesive layers;
- optionally attaching the flexible motion sensor to various wearable devices such as glove, sleeves, or jackets, made up of textiles or polymers; and
- monitoring resistance changes in response to body movements.

A flexible motion sensor as disclosed herein works at a low voltage and a low frequency.

DETAILED DESCRIPTION

Figure 1:
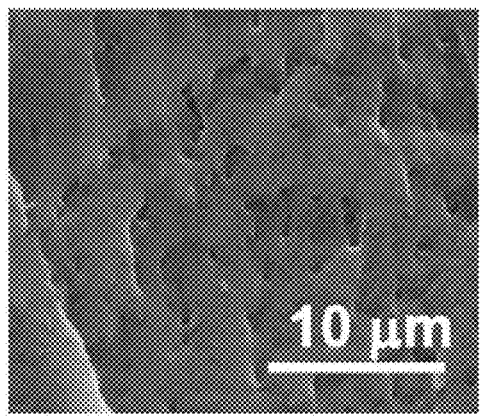
FIG. 1 shows three examples of cross-sectional Scanning Electron Microscopic (SEM) images, where the difference in layered structures between 0% (a), 6% (b), and 12% (c) laponite can be observed.
Figure 1:
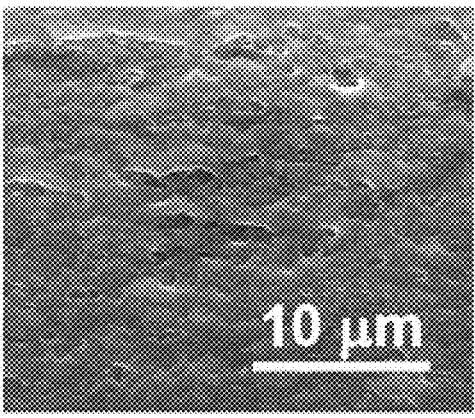
Figure 1:
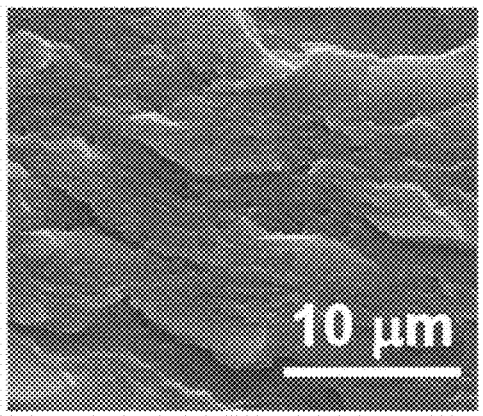

The description herein of any aspect or embodiment using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context, e.g. a composition described herein as comprising a particular element should be understood as also describing a composition consisting of that element, unless otherwise stated or clearly contradicted by context. It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

As used herein, the singular forms "a," "an," and "the" are intended to include the plural forms, including "at least one," unless the content clearly indicates otherwise. "At least one" is not to be construed as limiting "a" or "an."

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims and/or aspects appended hereto as permitted by applicable law.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined in the present specification.

In one or more embodiments, the electrolyte is a zwitterion.

In one or more embodiments, the electrolyte is a salt.

In one or more embodiments the salt is selected from the group of potassium chloride, sodium chloride, lithium chloride, calcium chloride, magnesium chloride, or a combination hereof.

In one or more embodiments, the electrolyte is in an amount high enough to make the material conductive.

In one or more embodiments, the electrolyte is present in an amount above 2 parts by weight for every 100 parts by weight of the silk fibroin.

In one or more embodiments, the electrolyte is present in an amount of 2.5 to 15 parts by weight for every 100 parts by weight of the silk fibroin.

In one or more embodiments, the electrolyte is present in an amount of 2.5 to 15 parts, such as 3.5 to 10 parts, such as 4 to 8 parts, such as 4 to 6 parts by weight for every 100 parts by weight of the silk fibroin.

In one or more embodiments, the electrolyte is present in an amount of 5 parts by weight for every 100 parts by weight of the silk fibroin.

In one or more embodiments, the nanomaterial is a nano clay, a carbon nanomaterial, a Mxene or a combination hereof. The carbon nanomaterial may be selected from the group of graphene, carbon nanotubes or a combination hereof.

By Mxene is normally meant a two dimensional nanomaterial comprising a multiple of arrangements of carbides, nitrides and transition metals, such as molybdenum or titanium.

Nano clay may be described as a nacre-mimetic nanomaterial with two-dimensions. Nano clays are a type of layered silicates with nonmetric thickness and diameter in the nano range. These nano plates have previously shown many applications such as antibacterial activity, sterilizing effect, adsorption of toxins, and membrane coating. The incorporation of nano clays into polymeric matrixes could enhance the mechanical, physical, and barrier properties of polymers. Montmorillonite and kaolinite are examples of nano clays that have been used as fillers in food systems.

Depending on chemical composition and nanoparticle morphology, nano clays are organized into several classes such as montmorillonite, bentonite, kaolinite, hectorite, and halloysite.

In one or more embodiments, the nano clay is selected from the group of montmorillonite, bentonite, kaolinite, hectorite, halloysite, or a combination hereof.

In one or more embodiments, the nano clay is hectorite.

In one or more embodiments, the hectorite is laponite.

Laponite is a synthetic clay mineral known to have widespread applications as a rheology modifier and as a reinforcement in a variety of industries such as mining, petroleum, home and personal care, pharmaceutical, agrochemical, and paint polymer. The primary particle of laponite possesses anisotropic nanometric shape that has dissimilar charge distribution.

Laponite has a chemical formula $Na_{0.7}Si_8Mg_{5.5}Li_{0.3}O_{20}(OH)_4$. Laponite particles are disk shaped with a thickness of 1 nm and diameter of 25±2 nm. In a single layer of laponite, two tetrahedral silica sheets sandwich one octahedral magnesia sheet. In the middle octahedral sheet few magnesium atoms are substituted by lithium atoms (isomorphic substitution) creating a deficiency of positive charge within the sheet. Consequently, in a dry state, the faces of laponite particles, that are electron rich, share the electrons with sodium atoms that reside in the interlayer space. Upon dispersing in the aqueous media, the $Na^+$ ions dissociate rendering a permanent negative charge to the faces of laponite particles. The edge of laponite particle predominantly contains MgOH groups from the octahedral magnesia sheets. The point of zero charge (PZC), for oxides and hydroxides of magnesium is above pH 10. According to manufactures of laponite, the edge of laponite particle, which contains predominantly MgOH, is positive below pH 11 indicating pH of 11 to be a point of zero charge for the edges of laponite particles (Applied Clay Science 97-98 (2014) 72-77).

In one or more embodiments, the nanomaterial is present in an amount of 6 to 20 parts, such 6 to 18 parts, such as 8 to 16 parts, or such as 10 to 14 parts by weight for every 100 parts by weight of the silk fibroin.

In one or more embodiments, the nanomaterial is present in an amount of 12 parts by weight for every 100 parts by weight of the silk fibroin.

In one or more embodiments, the nanomaterial is present in an amount of 6 to 20 parts, such 6 to 18 parts, such as 8 to 16 parts, or such as 10 to 14 parts by weight for every 100 parts by weight of the silk fibroin.

In one or more embodiments, the nanomaterial is present in an amount of 12 parts by weight for every 100 parts by weight of the silk fibroin.

In one or more embodiments, an optical transmittance of light through the flexible motion sensor material at a wavelength within the wavelength range between 400 nm and 800 nm is at least 50%, such as at least 60%, such as at least 70%.

In one or more embodiments, an optical transmittance of light through the touch panel material at a wavelength within the wavelength range between 400 nm and 800 nm is at least 50%, such as at least 60%, such as at least 70%.

In one or more embodiments, an optical transmittance of light through the ionic conductive, stretchable, and flexible transparent material at a wavelength within the wavelength range between 400 nm and 800 nm is at least 50%, such as at least 60%, such as at least 70%.

In one or more embodiments, an optical transmittance of light through the flexible motion sensor material at a wavelength above 400 nm is at least 50%, such as at least 60%, such as at least 70%.

In one or more embodiments, an optical transmittance of light through the touch panel material at a wavelength above 400 nm is at least 50%, such as at least 60%, such as at least 70%.

In one or more embodiments, an optical transmittance of light through the ionic conductive, stretchable, and flexible transparent material at a wavelength above 400 nm is at least 50%, such as at least 60%, such as at least 70%.

In one or more embodiments, a dimensional stability of the flexible motion sensor material has a thermal expansion coefficient between 25 ppm/K and 100 ppm/K, such as between 30 ppm/K and 80 ppm/K, such as between 40 ppm/K and 60 ppm/K, such as between 40 ppm/K and 50 ppm/K.

In one or more embodiments, a dimensional stability of the touch panel material has a thermal expansion coefficient between 25 ppm/K and 100 ppm/K, such as between 30 ppm/K and 80 ppm/K, such as between 40 ppm/K and 60 ppm/K, such as between 40 ppm/K and 50 ppm/K.

In one or more embodiments, a dimensional stability of the ionic conductive, stretchable, and flexible transparent material has a thermal expansion coefficient between 25 ppm/K and 100 ppm/K, such as between 30 ppm/K and 80 ppm/K, such as between 40 ppm/K and 60 ppm/K, such as between 40 ppm/K and 50 ppm/K.

In one or more embodiments, the flexible motion sensor material has a thermostability between 260° C. and 290° C., such as between 270° C. and 280° C., when measured via thermogravimetric analysis (TGA).

Thermogravimetric analysis (TGA) is a method of thermal analysis in which the mass of a sample is measured over time as the temperature changes. TGA is conducted on an instrument referred to as a thermogravimetric analyzer. A thermogravimetric analyzer continuously measures mass while the temperature of a sample is changed over time. Mass, temperature, and time in TGA are considered base measurements while many additional measures may be derived from these three base measurements. The thermogravimetric data collected from a thermal reaction is compiled into a plot of mass or percentage of initial mass on the y-axis versus either temperature or time on the x-axis. This plot is referred to as a TGA curve.

In one or more embodiments, the touch panel material has a thermostability between 260° C. and 290° C., such as between 270° C. and 280° C., when measured via thermogravimetric analysis (TGA).

In one or more embodiments, the ionic conductive, stretchable, and flexible transparent material has a thermostability between 260° C. and 290° C., such as between 270° C. and 280° C., when measured via thermogravimetric analysis (TGA).

In one or more embodiments, the flexible motion sensor material has a crystallization temperature between 230° C. and 250° C., such as between 240° C. and 250° C., when measured via differential scanning calorimetry (DSC).

Differential scanning calorimetry (DSC) is a thermoanalytical technique in which the difference in the amount of heat required to increase the temperature of a sample and reference is measured as a function of temperature. Both the sample and reference are maintained at nearly the same temperature throughout the experiment. The temperature program for a DSC analysis is designed such that the sample holder temperature increases linearly as a function of time. The reference sample should have a well-defined heat capacity over the range of temperatures to be scanned. The basic principle underlying this technique is that when the sample undergoes a physical transformation such as phase transitions, more or less heat will need to flow to it than the reference to maintain both at the same temperature. Whether less or more heat must flow to the sample depends on whether the process is exothermic or endothermic.

In one or more embodiments, the touch panel material has a crystallization temperature between 230° C. and 250° C., such as between 240° C. and 250° C., when measured via differential scanning calorimetry (DSC).

In one or more embodiments, the ionic conductive, stretchable, and flexible transparent material has a crystallization temperature between 230° C. and 250° C., such as between 240° C. and 250° C., when measured via differential scanning calorimetry (DSC).

In one or more embodiments, the flexible motion sensor material is dissolvable in a dissolving solution, the dissolving solution comprising:
  lithium bromide in a concentration of at least 8 molar, and
  optionally sodium hydroxide in a concentration of at least 0.3 molar.

In one or more embodiments, the touch panel material is dissolvable in a dissolving solution, the dissolving solution comprising:
  lithium bromide in a concentration of at least 8 molar, and
  optionally sodium hydroxide in a concentration of at least 0.3 molar.

In one or more embodiments, the ionic conductive, stretchable, and flexible transparent material is dissolvable in a dissolving solution, the dissolving solution comprising:
  lithium bromide in a concentration of at least 8 molar, and
  optionally sodium hydroxide in a concentration of at least 0.3 molar.

In one or more embodiments, the flexible motion sensor material is dissolvable in a dissolving solution, the dissolving solution comprising:
  lithium bromide in a concentration of at least 8 molar, and
  optionally sodium hydroxide in a concentration of at least 0.3 molar, wherein the dissolving solution is at a temperature of at least 40° C., such as at least 50° C., such as at least 60° C.

In one or more embodiments, the touch panel material is dissolvable in a dissolving solution, the dissolving solution comprising:
  lithium bromide in a concentration of at least 8 molar, and
  optionally sodium hydroxide in a concentration of at least 0.3 molar,
wherein the dissolving solution is at a temperature of at least 40° C., such as at least 50° C., such as at least 60° C.

In one or more embodiments, the ionic conductive, stretchable, and flexible transparent material is dissolvable in a dissolving solution, the dissolving solution comprising:
  lithium bromide in a concentration of at least 8 molar, and
  optionally sodium hydroxide in a concentration of at least 0.3 molar,
wherein the dissolving solution is at a temperature of at least 40° C., such as at least 50° C., such as at least 60° C.

In one or more embodiments, the flexible motion sensor material has a tensile strength of at least 10 MPa when measured with an Instron mechanical tester.

Instron is a manufacturer of test equipment designed to evaluate the mechanical properties of materials and components, such as universal testing machines. A universal testing machine (UTM—an Instron mechanical tester), also known as a universal tester, materials testing machine, or materials test frame, is used to test the tensile strength and compressive strength of materials. An earlier name for a tensile testing machine is a tensometer.

A specimen is placed in the machine between the grips and the grips are pulled apart while measuring the stress applied and the distance moved. This measures how strong it is (tensile strength) how stretchable it is (stretched length before breaking), and how stiff it is (Young Modulus).

In one or more embodiments, the touch panel material has a tensile strength of at least 10 MPa when measured with an Instron mechanical tester.

In one or more embodiments, the ionic conductive, stretchable, and flexible transparent material has a tensile strength of at least 10 MPa when measured with an Instron mechanical tester.

In one or more embodiments, the flexible motion sensor material has a Young Modulus of at least 2.0 GPa when measured with an Instron mechanical tester.

In one or more embodiments, the touch panel material has a Young Modulus of at least 2.0 GPa when measured with an Instron mechanical tester.

In one or more embodiments, the ionic conductive, stretchable, and flexible transparent material has a Young Modulus of at least 2.0 GPa when measured with an Instron mechanical tester.

In one or more embodiments, the flexible motion sensor material has a maximum strain before breakage of at least 1.5% when measured with an Instron mechanical tester.

In one or more embodiments, the touch panel material has a maximum strain before breakage of at least 1.5% when measured with an Instron mechanical tester.

In one or more embodiments, the ionic conductive, stretchable, and flexible transparent material has a maximum strain before breakage of at least 1.5% when measured with an Instron mechanical tester.

In one or more embodiments, the dissolving solution further comprises sodium hydroxide in a concentration of at least 0.3 molar.

In one or more embodiments, the dissolving solution is heated to a temperature of at least 40° C., such as at least 50° C., such as at least 60° C., prior to adding the ionic conductive, stretchable, and flexible transparent material to the dissolving solution.

In one or more embodiments, the dissolving solution is heated to a temperature of at least 40° C., such as at least 50° C., such as at least 60° C., after adding the ionic conductive, stretchable, and flexible transparent material to the dissolving solution.

In one or more embodiments, the touch panel surface area has a square shape and wherein the touch panel further comprises at least three, four, five, six, seven or eight electrodes connected to and positioned at opposite corners or edges of the touch panel.

In one or more embodiments, further comprising a controller calculating the location of touch based on the change in current from the electrodes.

In one or more embodiments, an electric sensitivity is unchanged when bending the touch panel material from a plane surface, such as 0 degrees, to a u-shaped surface, such as 180 degrees.

In one or more embodiments, an electric sensitivity is unchanged when touching the touch panel material a multiple of times, such as 100 times, such as 1,000 times, such as 10,000 times, such as 100,000 times, such as 1,000,000 times.

In one or more embodiments, the flexible motion sensor further comprises at least one selected from the group of a silver paste, a copper wire, a cloth adhesive tape, or combinations hereof.

In one or more embodiments, the motion sensor is cable of detecting changes in the flexible motion sensor material when bending the flexible motion sensor material from a plane surface, such as 0 degrees, all the way to a u-shaped surface, such as ±180 degrees.

In one or more embodiments, the motion sensor is cable of detecting changes in the flexible motion sensor material when gradually bending the flexible motion sensor material in from a plane surface, such as 0 degrees, all the way to a u-shaped surface, such as ±180 degrees, such as bending from 0 degrees to 30 degrees to 80 degrees.

In one or more embodiments, the joint is a shoulder joint, a wrist joint, a finger joint, an elbow joint, a knee joint, or an ankle joint.

In one or more embodiments, the motion sensor can be attached to a glove or any wearable devices to use in various sectors such as health care, gaming, or sportswear. It can also be used on shoes to help runners improve their performances.

In one or more embodiments, the motion sensor can be attached to a glove to use in training as a training tool for training surgeons.

In one or more embodiments, the motion sensor can be attached to a glove to use in assessing Parkinson's disease. A glove may be worn at home by a patient for a longer time period, e.g. one or more days, during which the shaking connected to Parkinson's disease comes and goes. By monitoring the frequency and strength of the shaking, health care personal is able to obtain information allowing them to assess the effect of e.g. Parkinson's disease medicine and its effect.

In one or more embodiments, further comprising a step of hydrating the obtained conductive, stretchable, and flexible transparent material with deionized water or a 2 molar lithium chloride solution.

When describing the embodiments, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisage all possible combinations and permutations of the described embodiments.

The present invention is further illustrated by the following examples, which are not to be construed as limiting the scope of protection. The features disclosed in the foregoing description and in the following examples may, both separately or in any combination thereof, be material for realizing the invention in diverse forms thereof.

EXAMPLES

Various examples are described hereinafter with reference to the figures. It should also be noted that the figures are only intended to facilitate the description of the examples. They are not intended as an exhaustive description of the claimed invention or as a limitation on the scope of the claimed invention. In addition, an illustrated example needs not have all the aspects or advantages shown. An aspect or an advantage described in conjunction with a particular example is not necessarily limited to that example and can be practiced in any other examples even if not so illustrated, or if not so explicitly described.

Example 1—Extraction of Silk Fibroin

Silk fibroin was extracted from *Bombyx Mori* silk cocoons. Briefly, 10 g of sliced silk cocoons were boiled in an aqueous solution of 0.02 M sodium carbonate (Sigma-Aldrich) for 30 minutes in order to remove all traces of sericin. The obtained silk fibroin fibers were subsequently dried at room temperature for 24 hours. The fibroin fibers were then dissolved in 9.3 M lithium bromide (Honeywell) at 60° C. for 6 hours and dialyzed against deionized water for 3 days. Finally, the fibroin solution was centrifuged for 20 minutes (three times) at 12000 rpm and 4° C. to remove any impurities.

Example 2—Preparation of SiPo (Silk Laponite) Thin Films

In order to prepare SiPo films, the silk fibroin solution of example 1 was diluted to 2.7% wt/vol in 25 ml MQ water. The pH of the solution was adjusted to 11 with 0.35 M ammonium hydroxide solution (28.0-30.0%, Sigma-Aldrich) and 10 mM potassium chloride (KCl, Sigma-Aldrich), and different concentrations (0%, 3%, 6%, 12% and 18%) of laponite RD (BYK additives, UK) were incorporated into the silk solution. The finalized solution was subsequently casted onto a plastic petri dish and dried at 40° C. for 24 hours.

Example 3—Characterization of the Thin Films—Cross-Sectional Images

Cross-sectional images of the SiPo films of example 2 were obtained from a FEI Quanta 200 ESEM FEG Scanning Electron Microscopy (SEM, USA) fitted with field emission gun electron source, in which the acceleration voltage was set at 10 kV and emission current at 10 mA. All SiPo films were cut, mounted on SEM stub and sputter coated with gold (10 nm) prior to the SEM imaging. Three examples of cross-sectional images are shown in FIG. 1, where the difference in layered structures between 0% (a), 6% (b), and 12% (c) laponite can be observed. In the SiPo film with low laponite content, globular clusters were observed in the cross sectional SEM images, while the incorporation of more laponite induced the formation of layer-by-layer structures. The composites prepared with higher amount of laponite (above 12%), are stacked together and form a layer-by-layer structure. These, kind of layered structures are advantage from a mechanical and barrier property point of view.

Example 4—Characterization of the Thin Films—FTIR

Figure 2:
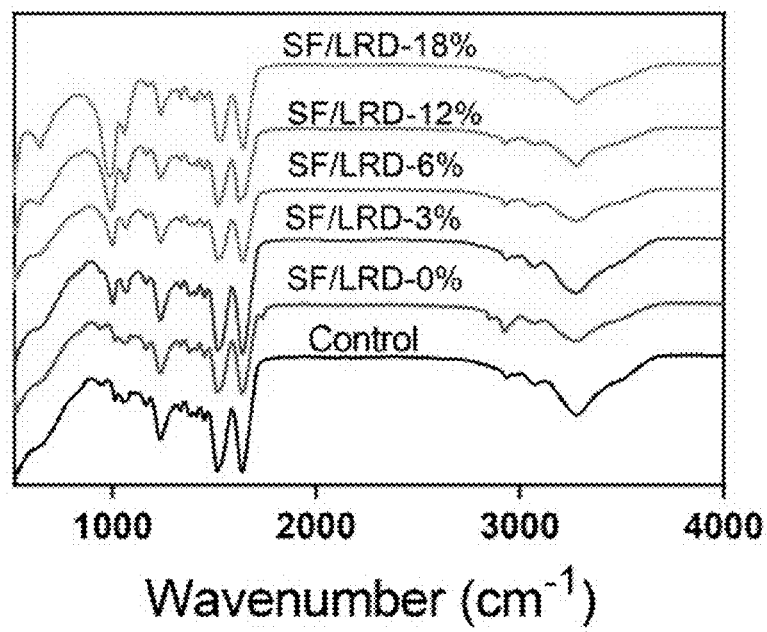
FIG. 2 shows the results of FTIR analysis (a) and examination of the secondary structure of 6% laponite (b) and 18% laponite (c).
Figure 2:
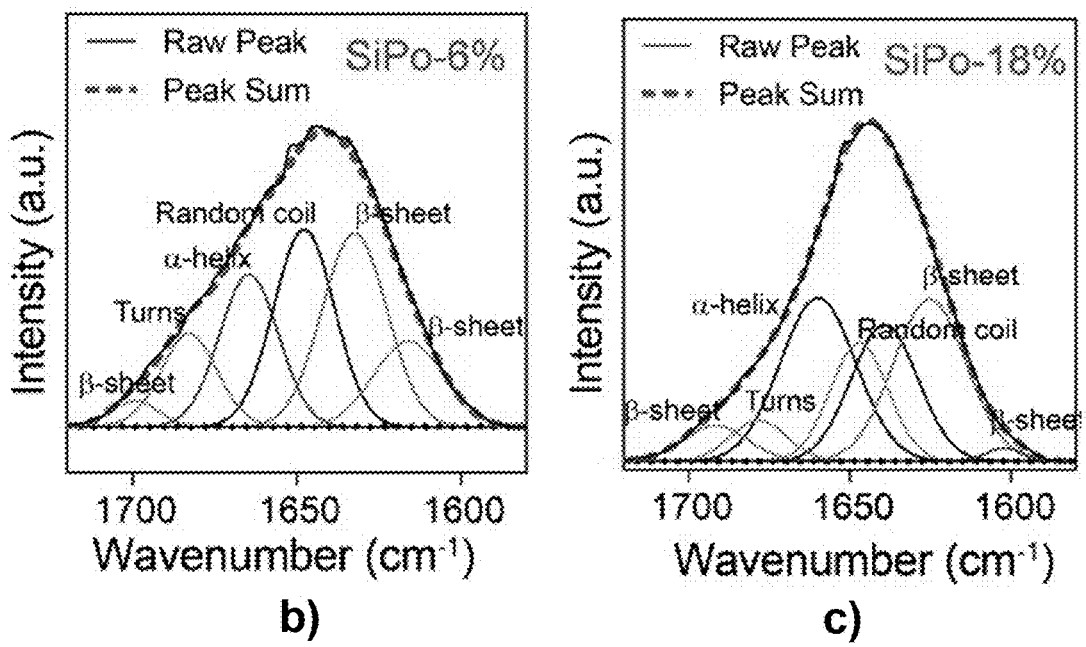

Fourier transform infrared (FTIR) spectroscopy was acquired using a PerkinElmer Spectrum 100 FTIR spectrometer (USA) equipped with a diamond crystal attenuated total reflectance (ATR) accessory. The transmittance spectra were collected at 25° C. over the range of 4000-500 cm$^{-1}$ with 16 scans at a resolution of 4 cm$^{-1}$. To examine the secondary structure of the silk proteins, the Amide I region was used. The absorbance spectra of the Amide I region (1580-1750 cm$^{-1}$) was deconvoluted using Origin Pro 2016 (OriginLab Corp.). To this end, absorption spectra's were baseline corrected and fitted with Gaussian-like peaks with a half-bandwidth of 25 cm$^{-1}$ using the PeakFit routine function within the Origin software. The results of FTIR analysis is shown in FIG. 2(a) and the results of the examination of the secondary structure of 6% laponite is shown in FIG. 2(b) and 18% laponite in FIG. 2(c). The control sample in the FTIR analysis is silk fibroin film without addition of salt at pH 7.

Example 5—Characterization of the Thin Films—Zeta Potential

Figure 3:
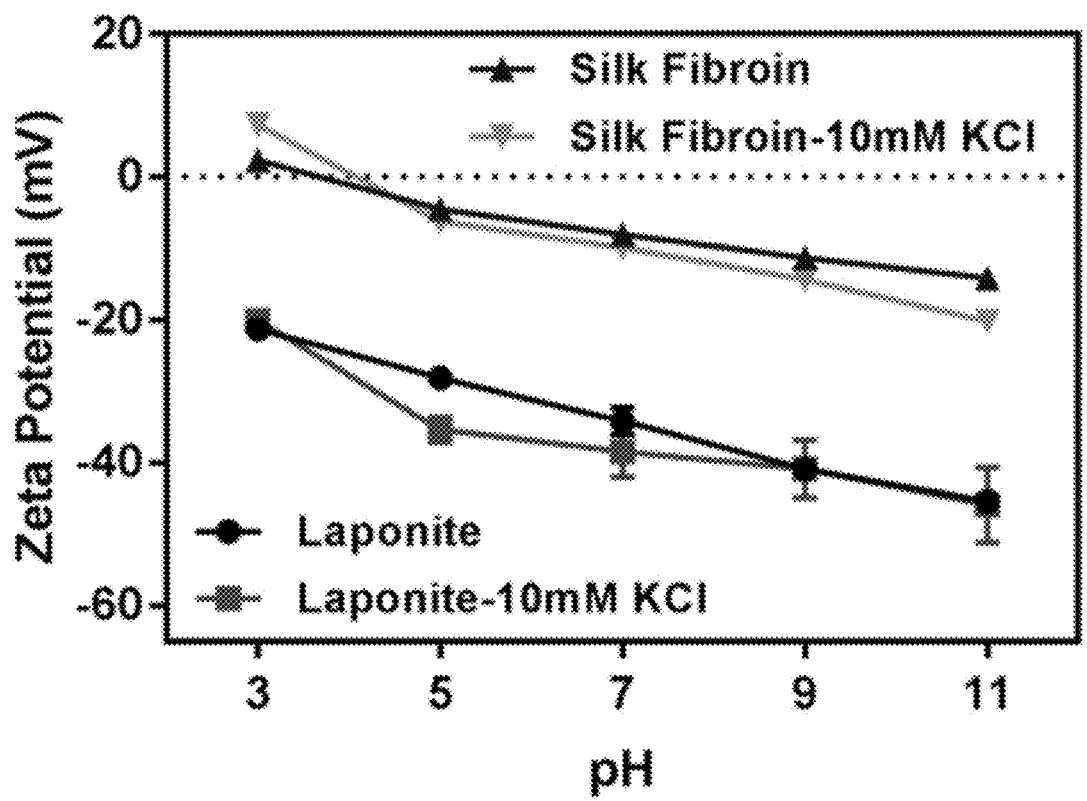
FIG. 3 shows the Zeta potential of silk fibroin and laponite solutions as a function of pH over an average of 10 measurements.

The Zeta potential of silk fibroin and laponite solutions was measured with a Malvern Zetasizer ZS apparatus (United Kingdom) equipped with a 4 mW HeNe laser operating at 632.8 nm. All measurements were performed at 25° C. for dilute solutions of silk fibroin and laponite by adjusting the pH of the solutions using NaOH and HCl. The values are reported as the average of 10 measurements and can be observed in FIG. 3. The zeta potential has been measured through the phase analysis light scattering technique and the obtained values are plotted as a function of pH in the range between 3 and 11. Silk fibroin is a polyampholyte with an isoelectric pH of approximately 4, and laponite displays a negative surface charge and a small positive rim charge. These two compounds can therefore potentially join into small agglomerates making it difficult to prepare a uniform and stable film. A study showed jellification of the SiPo film at acidic pH-values, which may be caused by a more positive charge distribution on the silk fibroin at lower pH-values, which will result in more intensified electrostatic interactions with the negatively charged surface of the laponite. This phenomena can be prevented by increasing the pH to generate a surplus of negative charge (decreasing zeta-potential) on the silk fibroin. Further the addition of potassium chloride (KCl) to the silk fibroin solution may further screen the electrostatic interactions.

Example 6—Optical Transparency of the Thin Films

Figure 4:
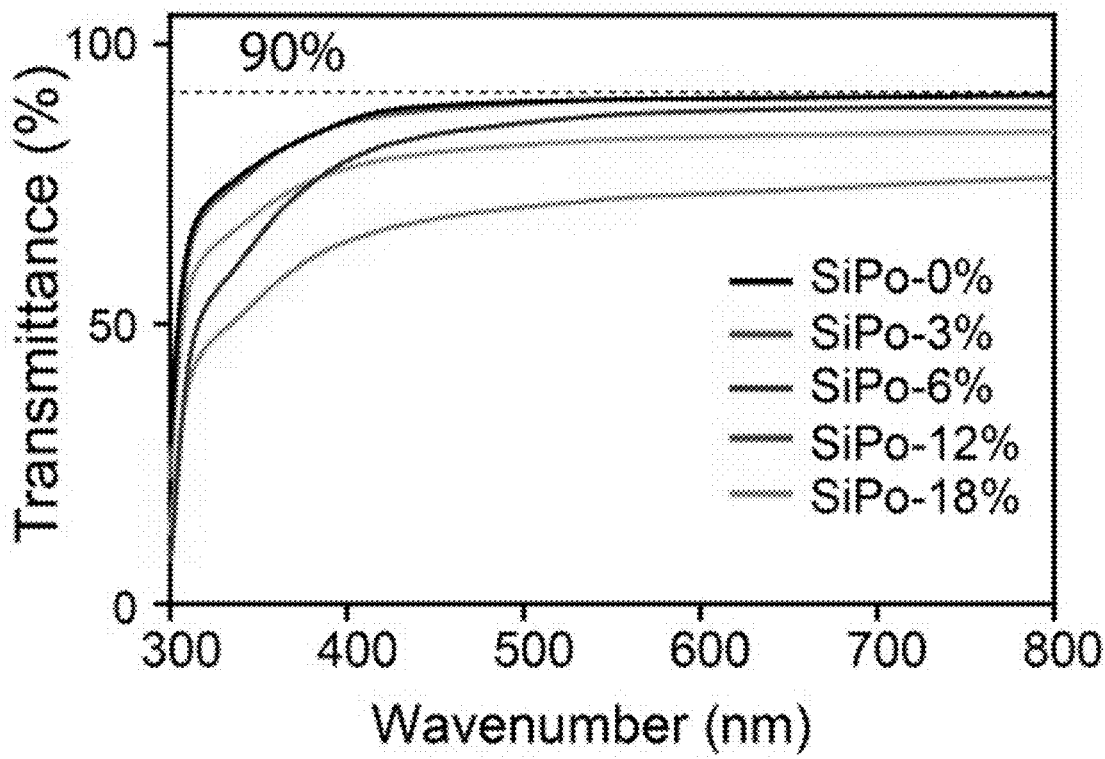
FIG. 4 shows UV-Vis spectroscopic analysis transmittance spectra between 300 and 800 nm of silk fibroin and laponite films containing 0%, 3%, 6%, 12%, and 18% laponite.

To determine the optical transparency of the SiPo films, UV-Vis spectroscopic analysis were carried out using a Shimadzu UV-2600 series (Ver. 1.03) UV-Vis spectrophotometer (Japan). Specifically, the spectra were collected using UVProbe (Ver. 2.43) software by placing the SiPo films in a film holder (P/N 204-58909). The transmittance spectra were recorded using air as the reference between 300 and 800 nm at slow scan speed with 1 nm interval. The results can be observed in FIG. 4, where films containing 0%, 3%, 6%, 12%, and 18% laponite are all analyzed. FIG. 4 shows that most of the SiPo films exhibit high transparency without nano clay (transparency around 88% at 400 nm). The addition of nano clay also exhibit good transparency (transparency around or above 75% at 400 nm), except for SiPo-18%. Further addition of laponite above 18% shows slight decrease in transparency to 60% at 400 nm (results not shown).

Example 7—Thermal Stability of the Thin Films

Figure 5:
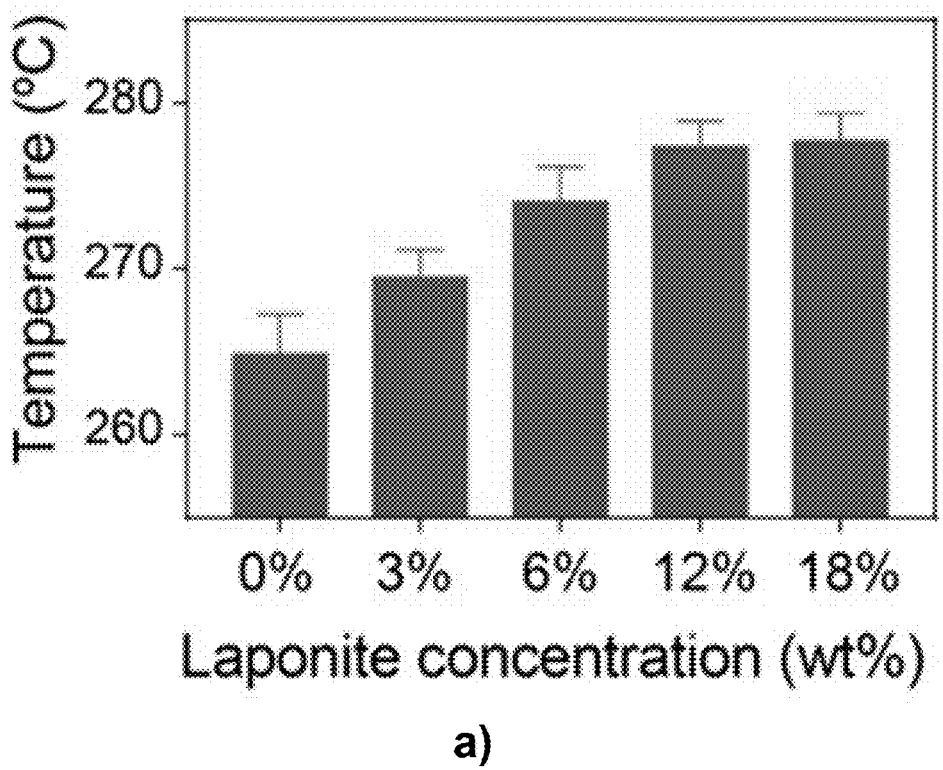
FIG. 5 shows thermal stability of the silk fibroin and laponite films (a) and the exothermic peak temperature between 200 and 250° C. (b).
Figure 5:
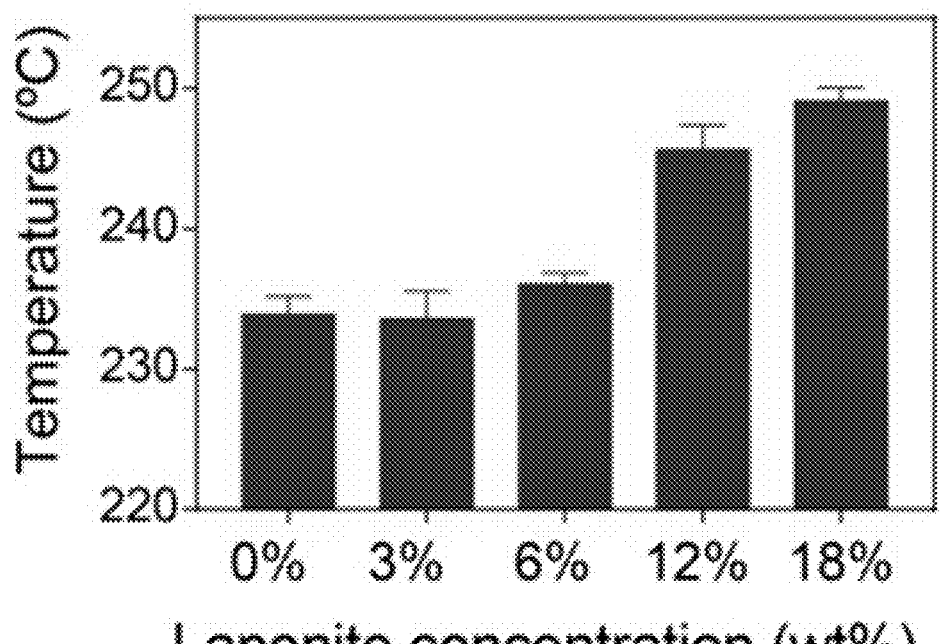

The thermal stability of our SiPo composite was characterized using TA TGA Q500 Thermogravimetric analyzer (TA instruments, USA) and a TA DSC Q200 Differential scanning calorimeter (TA instruments, USA). Thermogravimetric analysis (TGA) was carried out inside a nitrogen saturated chamber, by linearly increasing the quartz lined furnace temperature from 30° C. to 900° C. with the ramp of 10° C. min$^{-1}$ under nitrogen flow (60 mL min$^{-1}$). The mass loss as a function of temperature was monitored with an ultra-sensitive thermobalance. The onset temperature of the thermal decomposition in the range between 200 and 300° C. was determined using Universal analysis 2000 software (TA instruments) and reported as the thermal stability of the SiPo films. These values is shown in FIG. 5(a). Thermal stability is one of most important characteristic for polymeric films as a promising material in high performance electronics. The main thermal degradation of silk fibroin films is due the decomposition of the molecular back bone of the silk proteins starting around 250° C. The determined thermal stability is approximately at 265° C., which is increased to 278° C. by the addition of laponite concentration of 12% and above. The strong interfacial ionic bonding between laponite and the silk fibroin may be attributed as the key factor for enhanced thermal stability.

The differential scanning calorimetric (DSC) analysis were performed by increasing the chamber temperature linearly from 25 to 280° C. at the heating rate of 10° C. min$^{-1}$ under a dynamic nitrogen flow (50 mL min$^{-1}$). To record the DSC thermogram, the SiPo films were encapsulated into Tzero aluminum pans (Switzerland) and an empty Tzero pan was used as reference. The change in heat flow as a function of temperature was monitored. The exothermic peak temperature between 200 and 250° C. was reported as the crystallization temperature. These values is shown in FIG. 5(b). SiPo-0% film possesses a glass transition temperature (Tg) of 178° C., and displays a large endothermic peak at 227° C. as a result of non-isothermal crystallization of its amorphous chains. By addition of laponite an increased crystallization temperature is observed.

Example 8—Dimensional Stability of the Thin Films

Figure 6:
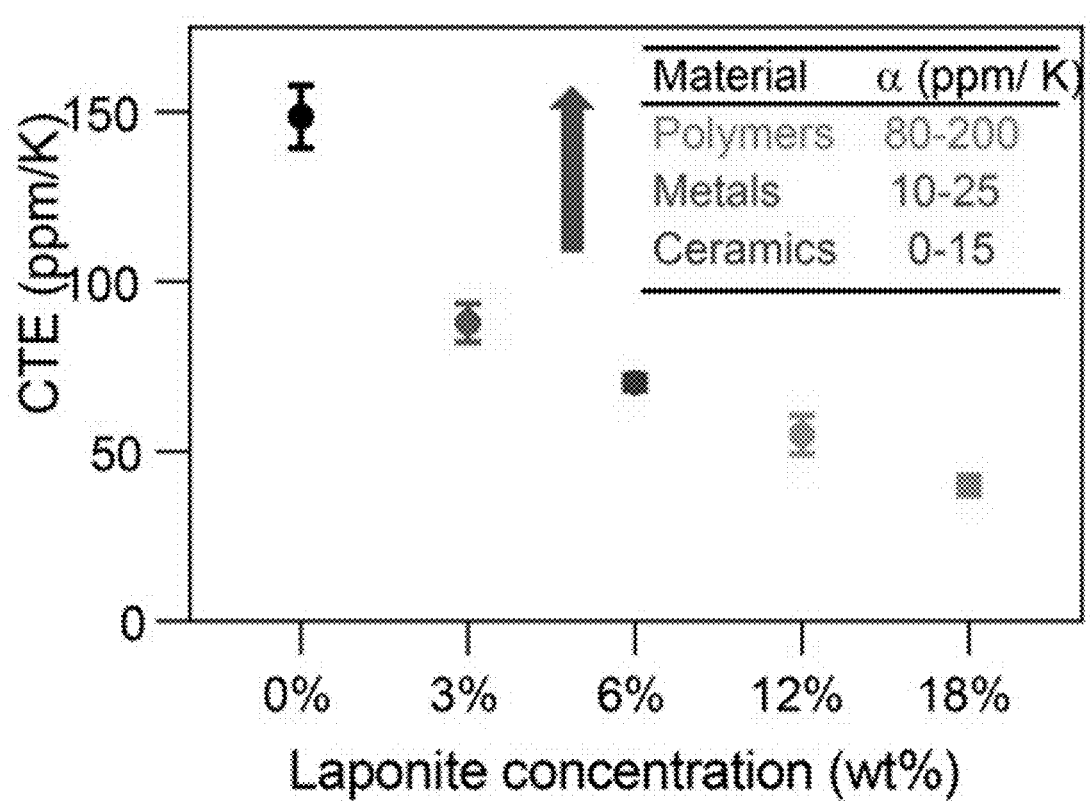
FIG. 6 shows the CTE values (Coefficient of Thermal Expansion values) from a slope of linear dimensional change in the temperature range of 25-75° C.

Dynamic temperature ramp test was performed using a RSA II Rheometrics solid analyzer (USA) to determine the coefficient of thermal expansion (CTE) of the SiPo films. The test was conducted on a 50 mm×5 mm films by increasing the temperature from 25 to 100° C. under nitrogen atmosphere with a heating rate of 5° C. min$^{-1}$. A constant force of 0.03N was applied in tensile mode at a frequency of 1.0 Hz and constant strain of 1.0%. The displacement in length (ΔL/L) as a function of temperature was collected using Rhios V4.3.2 software. CTE values were determined from the slope of the linear dimensional change in the temperature range of 25-75° C. These values are shown in FIG. 6. The CTE values are important in various sectors including electronics, where the thermal mismatch between the metal electrodes and the polymeric substrates cause dimensional shape changes and leads to failure of the components. The dimensional stability of the SiPo films is good and outcompetes that of conventional polymers as shown in FIG. 6. The CTE of the SiPo films are more similar to the value of metals. The CTE value of the silk fibroin films (150 ppm/K) decreased almost 3-fold as the laponite mass concentration increased from 0% to 18% and the value reached 40 ppm/K.

Example 9—Chemical Stability of the Thin Films

Figure 7:
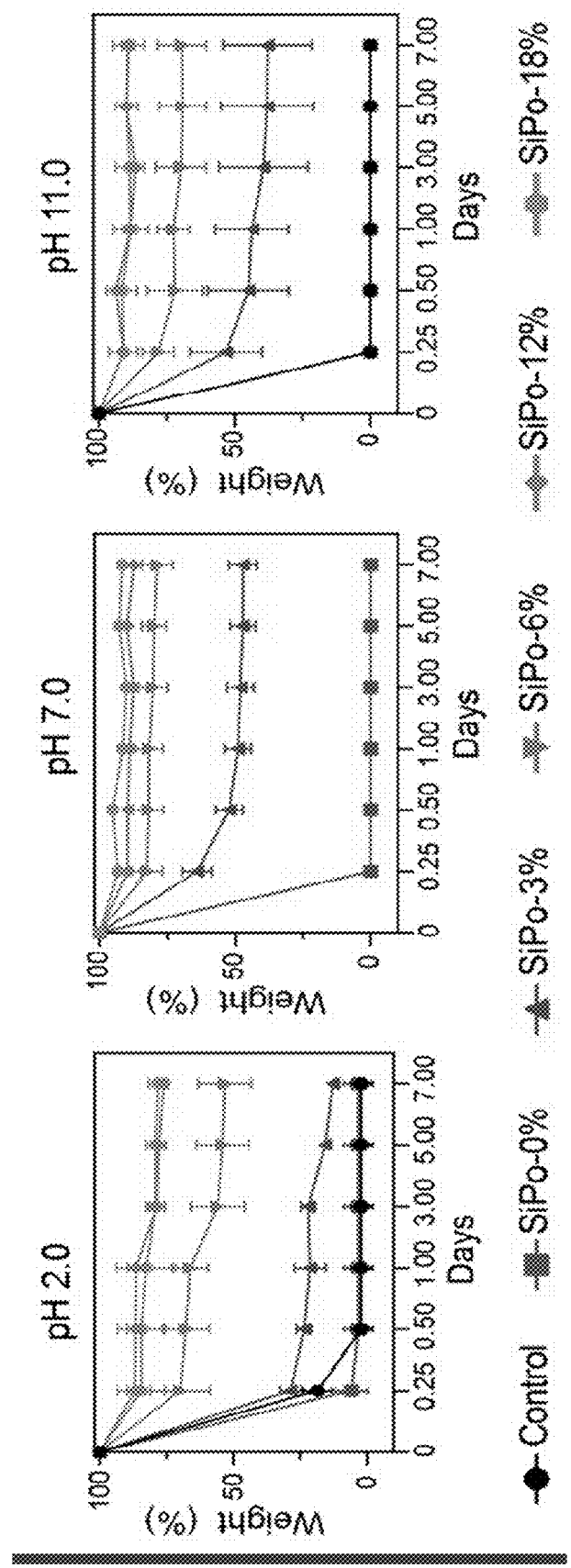
FIG. 7 shows the chemical stability of the silk fibroin and laponite films at different pH conditions.

Chemical Stability of the thin films were assessed in different pH condition using buffer solutions (pH 2.0 and pH 11.0) and deionized water (pH 7.0). The films (control, 0%, 3%, 6%, 12%, and 18%) were immersed in-to the respective solutions at room temperature and oven-dried at each time point. The dried weight of the samples was then recorded after 0.25, 0.5, 1, 3, 5 and 7 days and the weight loss was calculated using Eq. 1.

$$\text{Weight (\%)} = \frac{W_o(d) - W_t(d)}{W_o(d)} \times 100 \qquad \text{Eq. 1}$$

Where $W_o(d)$ is the initial dry weight and $W_t(d)$ is the dry weight of the samples at the respective time points. The results can be observed in FIG. 7. One obstacle for the integration of natural biopolymers into electronic applications is their instability with chemically demanding environments. In the case of silk, its secondary structure, which mainly consists of random coils and α-helices, makes it highly soluble in aqueous solutions. To enhance the stability of silk films at ambient conditions methods of increasing the β-sheet content have been pursued. Here is shown an increased β-sheet content through laponite incorporation, as well as the increased stability of these SiPo films both within aqueous environments and under harsh chemical conditions (pH 2 and pH 11). The control sample in the analysis is silk fibroin film without addition of salt at pH 7

Example 10—Mechanical Properties of the Thin Films

Figure 8:
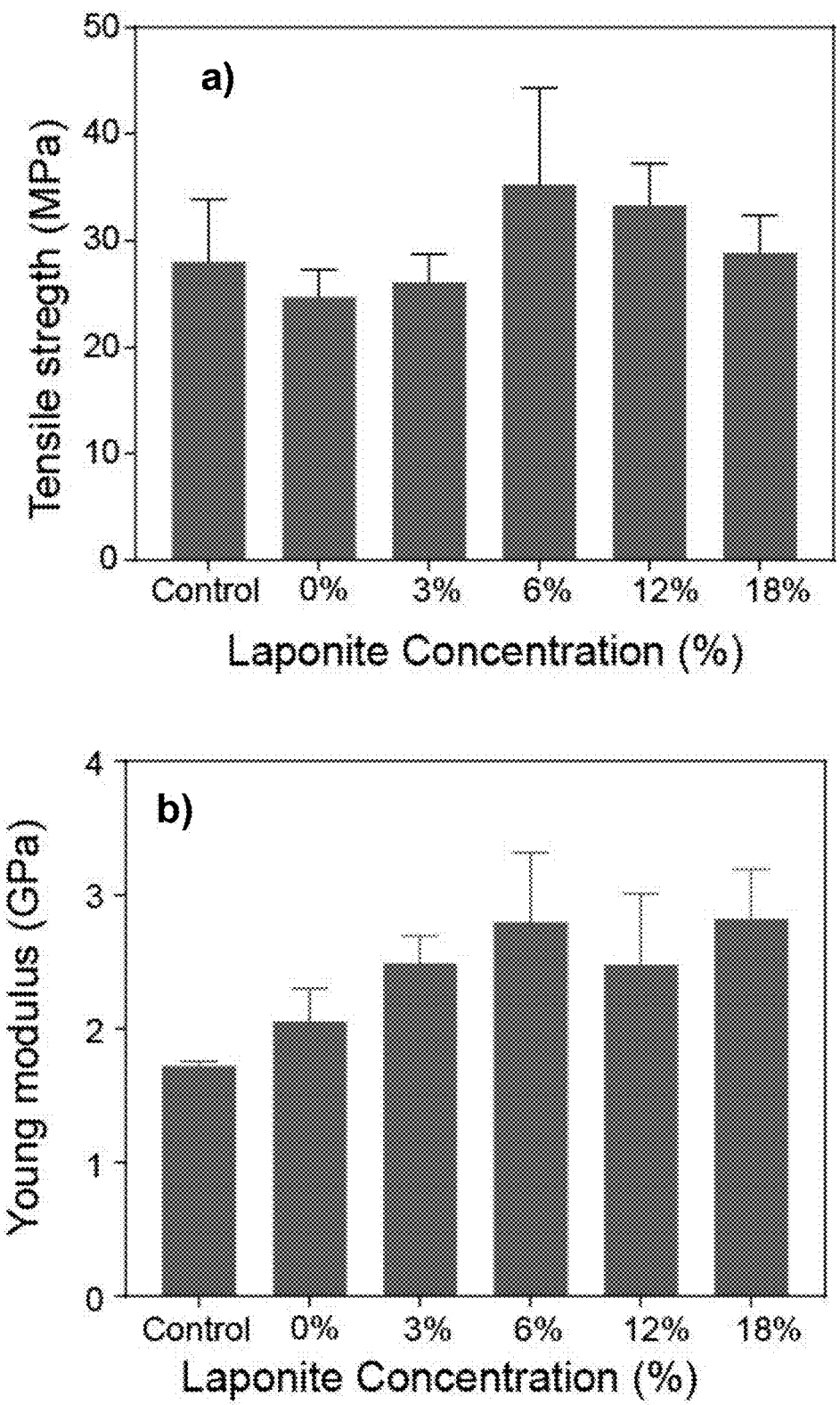
FIG. 8 shows the tensile strength (a), young modulus (b), strain break (c), and stress-strain curve (d) of a thin silk fibroin and laponite film comprising varying amounts of laponite.
Figure 8:
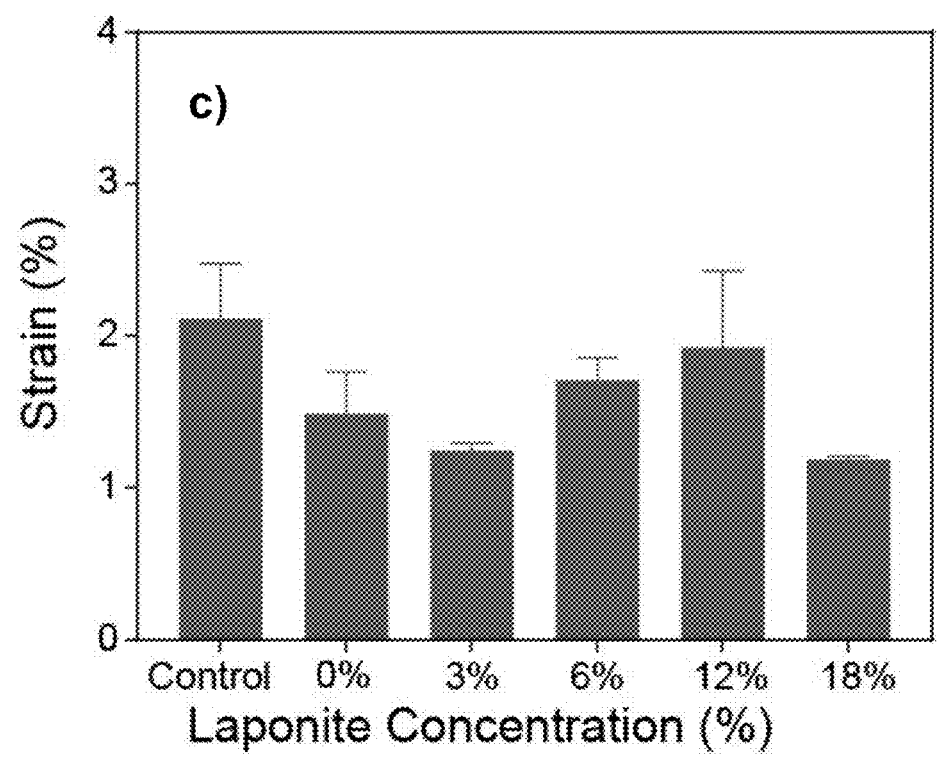
Figure 8:
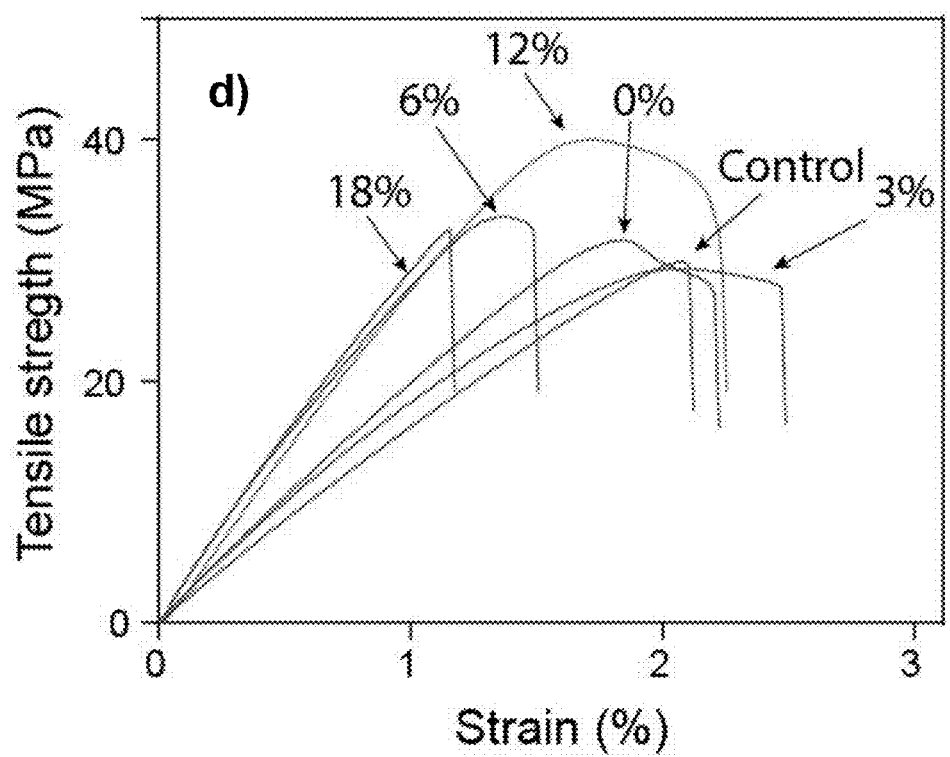

The mechanical properties of the composites were measured with an Instron 5967 mechanical testing machine. Samples were cut into 30 mm×2 mm pieces and the thickness of each film was measured using a calibrated digital electronic vernier caliper. The gauge length was set at 10 mm and the load and extension were balanced prior to the testing. The samples were strained at the rate of 1 mm min$^{-1}$ with a 500 N load-cell capacity until failure. Tensile strength, young modulus, and strain at break were calculated from the obtained stress-strain curve. The Young modulus was calculated by drawing a tangent to the initial linear portion of the stress-strain curve in the strain range between 0.0 and 0.4%. FIG. 8 shows the tensile strength (a), young modulus (b), strain break (c), and stress-strain curve (d) of a thin film comprising varying amounts of laponite RD.

Example 11—Recycling

The recycling of the SiPo films was examined in two steps. In the first step, 500 mg of the films were dissolved in 9.3M LiBr at 60° C. for 2 hours and followed by adding 0.5 M NaOH in order to increase the alkaline pH. The final solution was diluted 20 times with deionized water and was centrifuged at 12000 rpm for 20 min. The denser laponite layer was collected at the bottom and silk fibroin was remained in supernatant. The sediments were washed several times with deionized water and both sediment and supernatant were dialyzed against deionized water using 1 ml dialysis cassettes for 24 hours. The obtained solutions were dried at 60° C. and the presence of laponite and silk fibroin was confirmed by FTIR. The fluorescent laponite in the supernatant and sediment was also imaged using fluorescence microscopy. The fluorescence microscopy and FTIR spectroscopy were performed for pristine samples of laponite RD powder and freeze dried silk fibroin as control (data not shown). The recycling process of silk fibroin with laponite composites are safe and easy-to-use. Complete separation between the heavier laponite and more lightweight silk fibroin was achieved with this process.

Example 12—Ionic Conductivity

Figure 9:
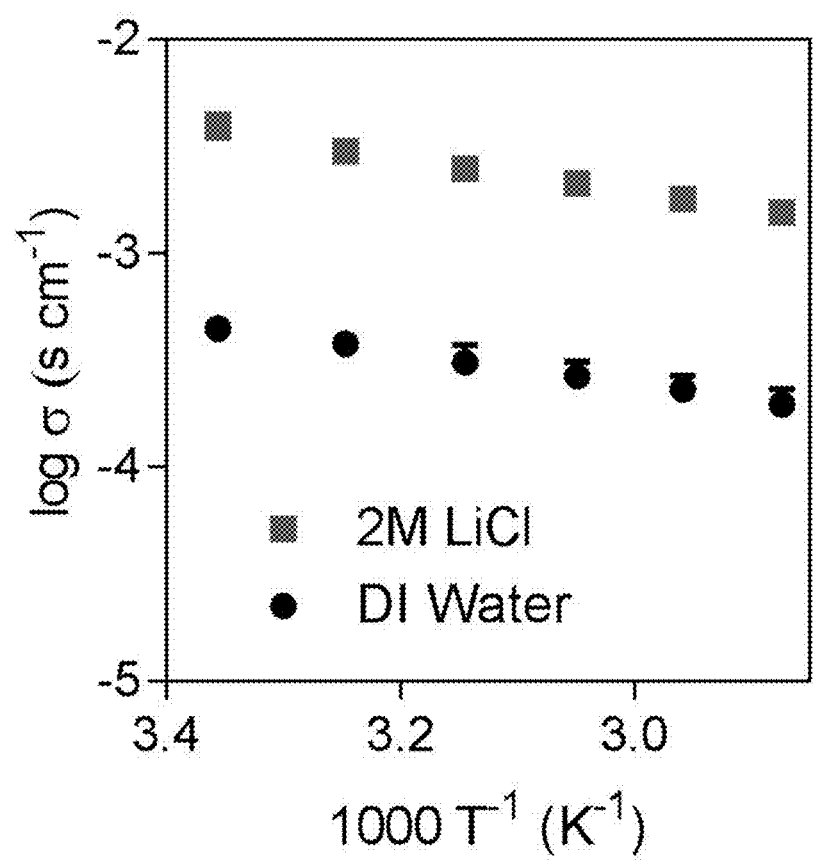
FIG. 9 shows the ionic conductivity ($\sigma$) of a thin silk fibroin and laponite film.

To study the ionic conductivity, SiPo films were immersed in aqueous solution of 2 M LiCl for 2 hours. The hydrated films were then dried gently using a piece of tissue paper. The electrochemical impedance spectroscopic (EIS) analysis was utilized to determine the ionic conductivity of the films. EIS analysis was performed using Gamry Potentiostat (Gamry Instruments, USA) at frequency range of 100 kHz to 10 Hz with amplitude of 10 mV. Samples of 1 cm$^2$ were sandwiched between two stainless steel plates and clamped in order to fabricate two electrode set up for EIS measurements. The stainless steel plates were then connected to the impedance analyzer and the set up were placed inside a jacketed reactor, equipped with water circulation system in order to control the temperature. Electrodes were stabilized at each temperature for 5 min prior to the measurements. Solution resistance (Rs) of the collected nyquist plot was determined using circular fitting at high frequencies using EC-Lab® software V11.10—Bio-Logic Science Instruments. The ionic conductivity of the samples was calculated according to Eq. 2:

$$\sigma = \frac{1}{R_s} \times \frac{l}{a} \qquad \text{Eq. 2}$$

where σ is the ionic conductivity, Rs is the solution resistance from the nyquist plot, l is the thickness of the sample and a is the sandwiched area. The results obtained can be seen in FIG. 9. These results show that SiPo films can be transformed into high fidelity capacitive touch sensors by simply dipping them into a lithium chloride (LiCl) solution, as LiCl ($\sim 10^{-3}$ Scm$^{-1}$) can increase the ionic conductivity compared to DI water ($\sim 10^{-4}$ Scm$^{-1}$). Even though, the ionic conductivity of the films slightly decreased at higher temperatures, the capacitive touch sensors can be operate at higher temperatures.

Example 13—Current Measurements of the Flexible Surface Capacitive Touch Panel

Figure 10:
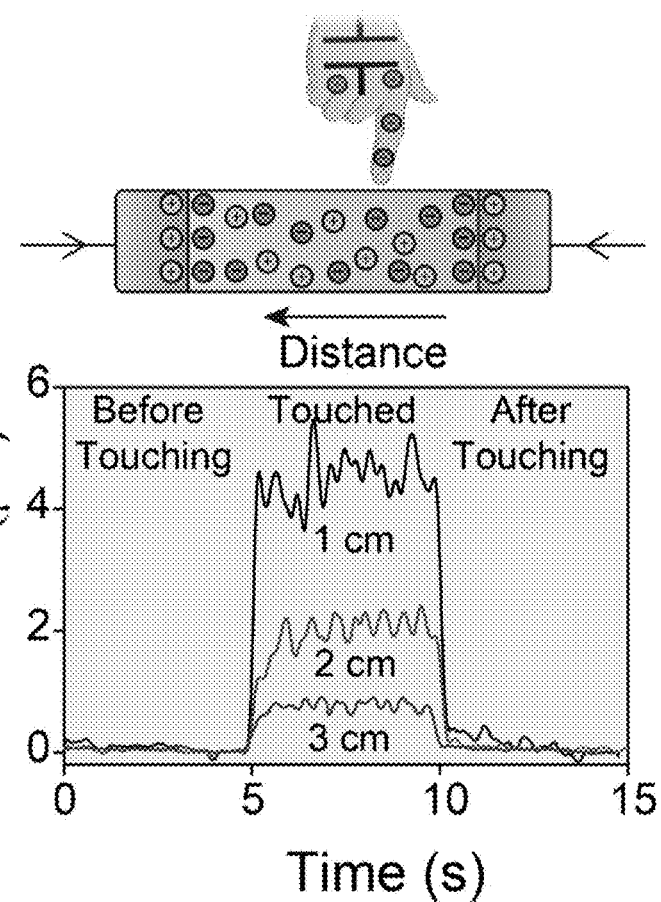
FIG. 10 shows current measurements on a touch panel, constructed from a silk fibroin and laponite ionic electrode, touched at different distances from the measuring electrode (a), the current divergence were a sample was touched with a finger (b), and the response of the touchscreen to bending angles (c).
Figure 10:
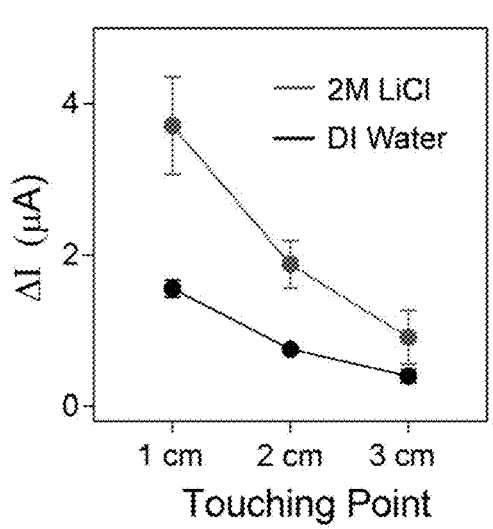
Figure 10:
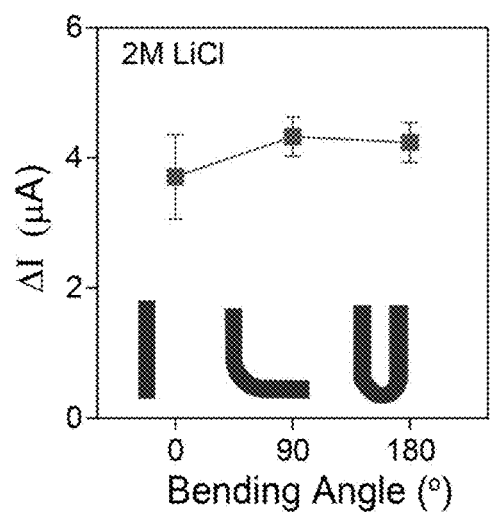

To perform the current measurement on touch panel, a SiPo ionic electrode was fabricated using 5 cm×1 cm ionic strips. Platinum plates were attached to both ends of the strips by applying silver epoxy paste by keeping electrode-to-electrode distance as 3 cm. These Pt electrodes were connected to an oscilloscope (Kesight MSOS104A mixed signal Oscilloscope 1 GHz, 20 Gsa/s, 10-bit ADC, Infiniium series) through a N2820A 3 MHz/Custom (1 μA) high sensitivity current probe (2-ch) with a user defined resistor tip (1Ω). To apply AC voltage at different frequencies, a function generator (Model 3312A, Hewlett Packard) was connected on both sides of the SiPo ionic system. The touch sensitivity of the touchscreen was measured at different frequencies ranging from 10 kHz to 40 kHz, using a function generator with an AC voltage ranging from −0.5 to 0.5 V. Prior to these sensitivity measurements samples were fixed with customized polymer clamps and the touch sensing capacity of the device was subsequently recorded by measuring the "finger touch" facilitated current change across the screen. The resultant AC current was recorded using Keysight oscilloscope and the absolute current and peak envelope was extracted using MATLAB 2016a. The current difference (ΔI) was calculated by subtracting baseline current from each value. In order to demonstrate the correlation between the touch-point location and the current, the one dimensional (1 D) ionic touchscreen was touched at different distances from the measuring electrode, as shows in FIG. 10(a). The resulting AC current was recorded using an oscilloscope and the magnitude in current difference (ΔI) was obtained with respect to distance. The results can be seen in FIG. 10(b). More specifically, a one-dimensional (1 D) SiPo strip (dipped in LiCl) was used to manufacture a Fleco-based touchscreen. A significant current response was observed when this ionic panel was touched with a human finger. This response was monitored at 10 kHz and measured with an oscilloscope. From the data presented in FIGS. 10(a) and (b), it's evident that a human touch can generate a measurable current response with a magnitude depending on the touch-point location. Therefore, one can use the magnitude of the current response to determine the coordinates of the touch-point. FIG. 10(b) shows that the slope is significantly steeper in LiCl than in DI water.

Furthermore, the response of touchscreen to bending angle was demonstrated in different bending angles such as 90° and 180° and the current divergence was monitored while the samples were touched with finger. These results can be seen in FIG. 10(c). These results show that the SiPo touchscreen is highly flexible, and the measured touch sensitivity remains almost the same even at a bending angle of 180°.

Example 14—Impedance Measurements of the Flexible Motion Sensor

Figure 11:
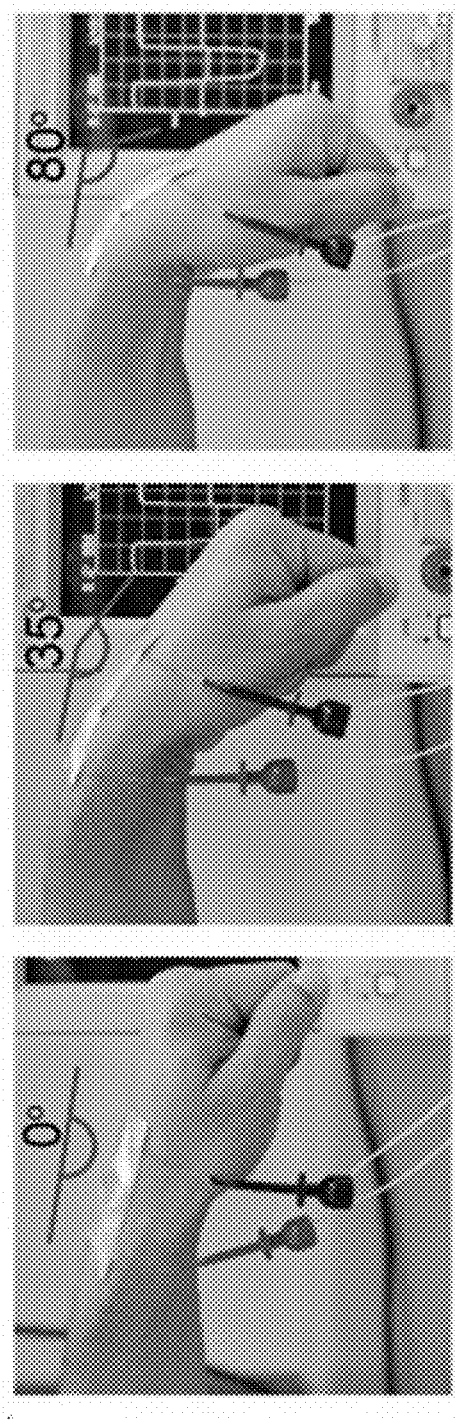
FIG. 11 shows the relative resistance ($\Delta R/R0$) (d) for a wrist at angles 0° (a), 35° (b), and 80° (c).
Figure 11:
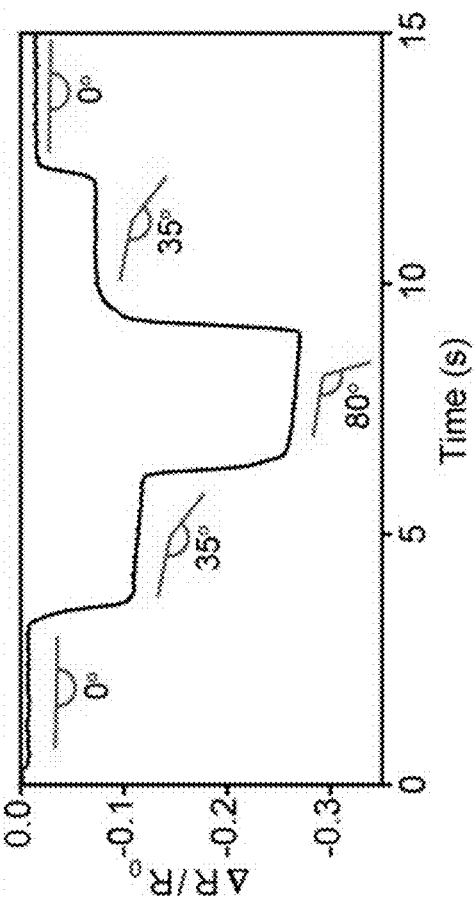
Figure 12:
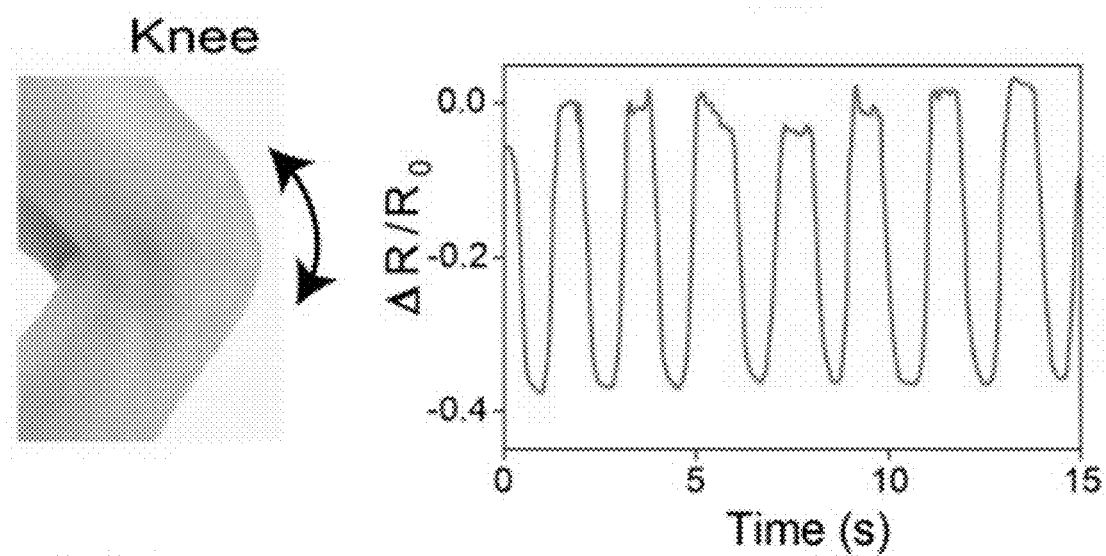
FIG. 12 shows the relative resistance ($\Delta R/R0$) for a moving knee.

SiPo 1D ionic strips, immersed in LiCl were investigated as a motion sensor. The motion-sensing device was fabricated by connecting copper wires to both ends of SiPo ionics using conductive silver epoxy paste. The sensor was attached to various moving parts of the body, such as finger, wrist, shoulder, ankle, elbow, and knee, using cloth adhesive tape, in order to minimize the drying effect of the SiPo ionics. The 1D ionic strips were varied in length (3 cm to 6 cm); depending on which part of the body they were applied to, but were kept constant in width (1 cm). The working-principle of the sensors was simple, as it relied on real-time monitoring of motion-facilitated changes in relative resistance. In this direction, the resistance change caused by body movement was monitored with an impedance apparatus (Agilent precision impedance analyzer 4294A, USA) operated with an AC voltage ranging from −0.5 to 0.5 V at 10 kHz. The relative resistance change of the SiPo ionic electrode was then recorded during the movement for the same parts of the human body. Relative resistance ($\Delta R/R_0$) was estimated from the resistance measurements, where $\Delta R$ is the difference between the resistance at each time point and the initial value ($R_0$). The results can be seen in FIG. 11(d) for a wrist at angles 0° (FIG. 11(a)), 35° (FIG. 11(b)), and 80° (FIG. 11(c)) (the impedance change was measured by holding the position for 2 seconds), and in FIG. 12 for a moving knee. From these results a significant resistance decrease is observed as the wrist is bent towards its flexion position (80°). Specifically, the rate of decrease significantly depended on the motion type that was monitored. Higher rates were observed when the wrist was moved from 35° to 80° than from 0° to 35°. Next, the motion-sensing experiments was extended to cover the locomotion of other important parts of the body such as finger, shoulder, elbow, knee and ankle. The impedance change from the moving knee is presented in FIG. 12. Interestingly, the resistance behavior of the sensor deferred significantly depending on the human motion as is evident from the body part-dependent signal patterns. This trend is most likely caused by the motion type/speed and electrical resistance, and could, therefore, in down-stream applications be employed to sense which part of the body is being moved.

What is claimed is:

1. An ionic conductive, stretchable, and flexible transparent material comprising silk fibroin, a nanomaterial, and an electrolyte, wherein the nanomaterial is present in an amount of 3 to 24 parts by weight for every 100 parts by weight of the silk fibroin, wherein the nanomaterial is a nano clay, a Mxene or a combination hereof.

2. The ionic conductive, stretchable, and flexible transparent material according to claim 1, wherein the electrolyte is present in an amount above 2 parts by weight for every 100 parts by weight of the silk fibroin.

3. The ionic conductive, stretchable, and flexible transparent material according to claim 1, wherein the nanomaterial further comprises a carbon nanomaterial.

4. The ionic conductive, stretchable, and flexible transparent material according to claim 1, wherein the nanomaterial is present in an amount of 6 to 20 parts.

5. The ionic conductive, stretchable, and flexible transparent material according to claim 1, wherein an optical transmittance of light through the ionic conductive, stretchable, and flexible transparent material at a wavelength above 400 nm is at least 50%.

6. The ionic conductive, stretchable, and flexible transparent material according to claim 1, wherein the ionic conductive, stretchable, and flexible transparent material is dissolvable in a dissolving solution, the dissolving solution comprising:
 lithium bromide in a concentration of at least 8 molar, and
 optionally sodium hydroxide in a concentration of at least 0.3 molar.

7. The ionic conductive, stretchable, and flexible transparent material according to claim 1, wherein the ionic conductive, stretchable, and flexible transparent material has a tensile strength of at least 10 MPa, and
 wherein the tensile strength is measured by pulling the material while measuring the stress applied and the distance moved.

8. A method of recycling an ionic conductive, stretchable, and flexible transparent material comprising silk fibroin, a nanomaterial, and an electrolyte, wherein the nanomaterial is present in an amount of 3 to 24 parts by weight for every 100 parts by weight of the silk fibroin wherein the nanomaterial is a nano clay, a Mxene or a combination hereof, and wherein the recycling method comprises the steps of:
 mixing a dissolving solution comprising lithium bromide in a concentration of at least 8 molar;
 adding the ionic conductive, stretchable, and flexible transparent material to the dissolving solution;
 dissolving the ionic conductive, stretchable, and flexible transparent material in the dissolving solution hereby creating a solid phase and a liquid supernatant phase;
 centrifuging the dissolving solution and collecting the supernatant phase wherein the silk fibroin is contained; and
 purifying the supernatant phase comprising the silk fibroin by dialysis against deionized water for at least 10 hours.

9. A flexible surface capacitive touch panel comprising a touch panel material defining a touch panel surface area, wherein the touch panel material comprises:
 silk fibroin;
 a nanomaterial, wherein the nanomaterial is present in an amount of 3 to 24 parts by weight for every 100 parts by weight of the silk fibroin, and
 an electrolyte, wherein the electrolyte is present in an amount above 2 parts by weight for every 100 parts by weight of the silk fibroin,
 wherein the nanomaterial is a nano clay, a Mxene or a combination hereof.

10. The flexible surface capacitive touch panel according to claim 9, wherein the touch panel surface area has a square shape and wherein the touch panel further comprises at least three electrodes connected to and positioned at opposite corners or edges of the touch panel.

11. The flexible surface capacitive touch panel according to claim 10, further comprising a controller calculating the location of touch based on the change in current from the electrodes.

12. A flexible motion sensor comprising a flexible motion sensor material defining a flexible motion sensor surface area, wherein the flexible motion sensor material comprises:
 silk fibroin,
 a nanomaterial, wherein the nanomaterial is present in an amount of 3 to 24 parts by weight for every 100 parts by weight of the silk fibroin, and
 an electrolyte, wherein the electrolyte is present in an amount above 2 parts by weight for every 100 parts by weight of the silk fibroin,
 wherein the nanomaterial is a nano clay, a Mxene or a combination hereof.

13. The flexible motion sensor according to claim 12, further comprising at least one selected from the group of a silver paste, a copper wire, a cloth adhesive tape, or combinations hereof.

14. A method for production of an ionic conductive, stretchable, and flexible transparent material comprising steps of:
 dissolving silk fibroin in a solution comprising lithium bromide to obtain a silk fibroin solution, wherein the lithium bromide is in a concentration above 8 molar;
 heating the silk fibroin solution to a temperature above 50° C. for at least 3 hours;
 dialyzing the silk fibroin solution against deionized water for at least 24 hours;
 centrifuging the silk fibroin solution to remove impurities and collecting the supernatant;
 adjusting the pH of the supernatant of the silk fibroin solution to a pH above 10;
 dissolving an electrolyte in the desired amount in the supernatant of the silk fibroin solution;
 dissolving a nanomaterial in the desired amount in the supernatant of the silk fibroin solution; and
 casting the silk fibroin solution at a required size at a temperature above 30° C. for at least 18 hours, hereby obtaining an ionic conductive, stretchable, and flexible transparent material comprising silk fibroin, the nanomaterial, and the electrolyte,
 wherein the nanomaterial is a nano clay, a Mxene or a combination hereof.

15. The method for production of an ionic conductive, stretchable, and flexible transparent material according to claim 14, further comprising a step of hydrating the obtained conductive, stretchable, and flexible transparent material with deionized water or a 2 molar lithium chloride solution.

16. A method for production of a flexible surface capacitive touch panel, the method comprising the step of:
 affixing at least two platinum or copper plates on the ionic conductive, stretchable, and flexible transparent material obtained by the method according to claim 14, using silver epoxy paste, hereby obtaining a flexible surface capacitive touch panel,
 wherein the flexible surface capacitive touch panel is adapted for operating at an AC voltage of −0.5 to 0.5 V and within a frequency range of 10 to 40 kHZ, wherein an AC current or capacitance response from a finger-touch is measureable using an oscilloscope.

17. A method for production of a flexible motion sensor comprising the steps of:
 connecting copper wires to both ends of the ionic conductive, stretchable, and flexible transparent material obtained by the method according to claim 14 using conductive silver epoxy paste, hereby obtaining a flexible motion sensor, wherein the flexible motion sensor is adapted for operating at 10 kHz by applying an AC voltage ranging from −0.5 to 0.5 V;
 attaching the flexible motion sensor to various moving parts of a body such as a finger, a wrist, a shoulder, an ankle, an elbow, or a knee, by means of cloth adhesive tape or adhesive layers;
 optionally attaching the flexible motion sensor to various wearable devices such as glove, sleeves, or jackets, made up of textiles or polymers; and monitoring resistance changes in response to body movements.

* * * * *